United States Patent [19]
Bille

[11] Patent Number: 5,920,373
[45] Date of Patent: Jul. 6, 1999

[54] METHOD AND APPARATUS FOR DETERMINING OPTICAL CHARACTERISTICS OF A CORNEA

[75] Inventor: Josef F. Bille, Heidelberg, Germany

[73] Assignee: Heidelberg Engineering Optische Messysteme GmbH, Heidelberg, Germany

[21] Appl. No.: 08/936,238

[22] Filed: Sep. 24, 1997

[51] Int. Cl.$^6$ ....................................................... A61B 3/10
[52] U.S. Cl. ............................................................ 351/212
[58] Field of Search ................................... 351/205, 206, 351/211, 212, 215, 246, 247, 221; 600/476, 558, 587

[56] References Cited

U.S. PATENT DOCUMENTS

| | | |
|---|---|---|
| 3,769,963 | 11/1973 | Goldman et al. . |
| 4,669,466 | 6/1987 | L'Esperance . |
| 4,732,148 | 3/1988 | L'Esperance, Jr. . |
| 4,770,172 | 9/1988 | L'Esperance, Jr. . |
| 4,773,414 | 9/1988 | L'Esperance, Jr. . |
| 4,907,586 | 3/1990 | Bille et al. . |
| 4,988,348 | 1/1991 | Bille . |
| 5,062,702 | 11/1991 | Bille . |
| 5,459,570 | 10/1995 | Swanson et al. . |
| 5,787,890 | 8/1998 | Reiter et al. ............................. 600/476 |
| 5,822,035 | 10/1998 | Bille ....................................... 351/215 |

FOREIGN PATENT DOCUMENTS

PCT/US92/03536  11/1992  WIPO .

*Primary Examiner*—George Manuel
*Attorney, Agent, or Firm*—Nydegger & Associates

[57] ABSTRACT

A system for determining the birefringent topography of a birefringent sample (e.g. cornea of an eye) includes a scanning tomopgraphy unit for establishing a plane of focus and an ellipsometer for generating a laser beam that is useable to obtain a birefringent measurement of the sample. The system also includes a topography unit for determining the angle the laser beam is incident on the sample, and a computer for correcting the birefringent measurement to account for this angle of incidence. A Z-tracker unit is used to maintain a proper relationship between system components during its operation. In a refinement of the system, where the sample is the cornea of an eye, the affects of patient heart beat and respiration can be preprogrammed into the computer for use in correcting the birefringent measurement.

25 Claims, 4 Drawing Sheets

METHOD AND APPARATUS FOR DETERMINING OPTICAL CHARACTERISTICS OF A CORNEA

FIELD OF THE INVENTION

The present invention pertains generally to optical diagnostic equipment and methods for their use. More specifically, the present invention pertains to diagnostic evaluations of the optical characteristics of the cornea of an eye. The present invention is particularly, but not exclusively, useful for creating a topography of the refractive power of a cornea which can be used to detect corneal diseases, or to plan for refractive surgery.

BACKGROUND OF THE INVENTION

Knowing the optical characteristics of a cornea can be very helpful to an ophthalmologist. Specifically, by knowing the refractive power of the cornea the ophthalmologist is able to diagnose certain corneal diseases, such as Keratokonus, and to properly plan for refractive surgical operations for the correction of such maladies as astigmatism and myopia. Heretofore, the determination of the refractive power of a cornea has been limited, and based solely on an evaluation of the front or anterior surface of the cornea. Such limited evaluations have, unfortunately, obtained a rather high level of unsatisfactory surgical results. It is clear that a more complete determination of the refractive topography of the cornea is necessary if a greater percentage of surgeries are to be successful. As can be easily appreciated, an evaluation of the entire cornea, rather than only its anterior surface, is both necessary and desirable.

Anatomically, the cornea of an eye comprises five discernible and distinct layers of tissue. Going inwardly from the anterior surface of the cornea to its posterior surface these layers are, in order: the epithelium; Bowman's membrane; the stroma; the endothelium; and Descemet's membrane. Of these, the stroma is, by far, the largest volume of tissue in the cornea. Consequently, the stroma is the most significant corneal tissue insofar as a contribution to the refractive power of the cornea is concerned. It follows, therefore, that surgical operations to alter the refractive power of the cornea should be undertaken with as much knowledge of the stromal contribution as is possible. Importantly, it is now known there are stress distributions within the stroma which, if unaccounted for, can lead to unpredictable results when they are relieved by an incision. Stated differently, the relaxation of stress distributions in the stroma by a corneal incision affects the surgical reshaping of the cornea.

It is known that stress distributions within the stroma result in birefringence. Further, it is known that the birefringent properties of the corneal stroma which result from these stresses are detectable. Consequently, by obtaining a topography of the intrinsic birefringence of the cornea, the stress distribution within the cornea can be ascertained. With this information, incisions can then be made into the cornea which will give more predictable results for the refractive power of the surgically corrected cornea.

To determine the birefringent topography of the cornea, measurements can be made by an ellipsometer of a type fully disclosed in U.S. application Ser. No. 08/709,243 which is incorporated herein by reference, and which is assigned to the same assignee as the present invention. These measurements, however, are affected by several factors. One such factor depends on the angle of incidence (θ) at which the ellipsometer's light beam enters the cornea relative to its anterior surface. In turn, the angle of incidence θ is affected by the curvature (topography) of the anterior corneal surface. Additionally, other factors which cause corneal movement, such as the patient's breathing, and the patient's heart beat, will have their effects and need to be considered. Thus, in order to obtain an accurate and precise birefringent topography which will be useful to the ophthalmologist for reshaping the cornea, the ellipsometer's birefringent measurements need to be corrected to properly account for these factors.

In light of the above it is an object of the present invention to provide a system and method for determining the birefringent topography of a cornea which accounts for local cornea curvature influences in the determination of the topography. It is another object of the present invention to provide a system and method for determining the birefringent topography of a cornea which accounts for the patient's heart beat and the patient's breathing in the determination of the topography. Yet another object of the present invention is to provide a system and method for determining the birefringent topography of a cornea which is easy to use, relatively simple to manufacture and comparatively cost effective.

SUMMARY OF THE PREFERRED EMBODIMENTS

A system and method for determining the birefringent topography of a birefringent sample (e.g. the cornea of an eye) includes an ellipsometer for making birefringent measurements of the sample. The system also includes components which are interactive with the ellipsometer to precisely correct the birefringent measurements for inaccuracies which are due to variations in the local curvature of the sample (cornea). More specifically, the associated components include a topography unit which analyzes wavefront measurements which are obtained from wavefronts that are reflected from the sample. With these measurements, the topography unit determines the sample surface (corneal) curvature, and the angle at which the laser beam from the ellipsometer is incident on this surface. Further, the associated components include a computer for revising the birefringent measurements of the ellipsometer to account for the measured angles of incidence.

In addition to the ellipsometer, the topography unit and the computer mentioned above, the system of the present invention includes a laser scanning tomography unit which is used to establish a plane of focus for the ellipsometer within the sample. Further, a Z-tracker unit is included which monitors movement of the birefringent sample so that, despite such movement, the focus of the ellipsometer can be maintained in the plane of focus. To do all of this, the Z-tracker unit establishes a base datum reference that is taken relative to the anterior surface of the birefringent sample (cornea). Deviations of the anterior surface from the base datum are then measured to generate error signals. In turn, the computer focuses the ellipsometer in a manner which minimizes these error signals. Thus, inaccuracies which might be introduced by unwanted eye movement are obviated. In a refinement of the system, the computer can also be preprogrammed to assist the Z-tracker unit by accounting for movements of the cornea which are due to the heart beat and the breathing of the patient.

In the operation of the system of the present invention, the laser scanning tomography unit of the system first establishes a plane of focus which is located within the birefringent sample (cornea). Preferably, when the birefringent properties of a cornea are being measured, the first plane of focus is located near the posterior surface of the cornea. Simultaneously, the Z-tracker unit establishes a reference base datum relative to the anterior surface of the cornea, and the computer locks in on the spatial relationship between the plane of focus and the base datum. The ellipsometer is then activated to generate a laser beam that is focused onto a point in the plane of focus. Once the ellipsometer is properly focused, the laser beam emanating from the ellipsometer is selectively polarized to sequentially obtain sixteen different readings from the point in the plane of focus. These sixteen readings are then collectively used as contributions to a measurement of the birefringent property of the material at the point of focus. As desired, this process can be repeated to obtain measurements for the birefringent properties of additional points in the plane of focus. Further, additional planes of focus can be established and a plurality of points measured in each of the planes. Thus, a birefringent topography for a volume in the birefringent sample can be generated and used by the operator for determining internal stresses.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
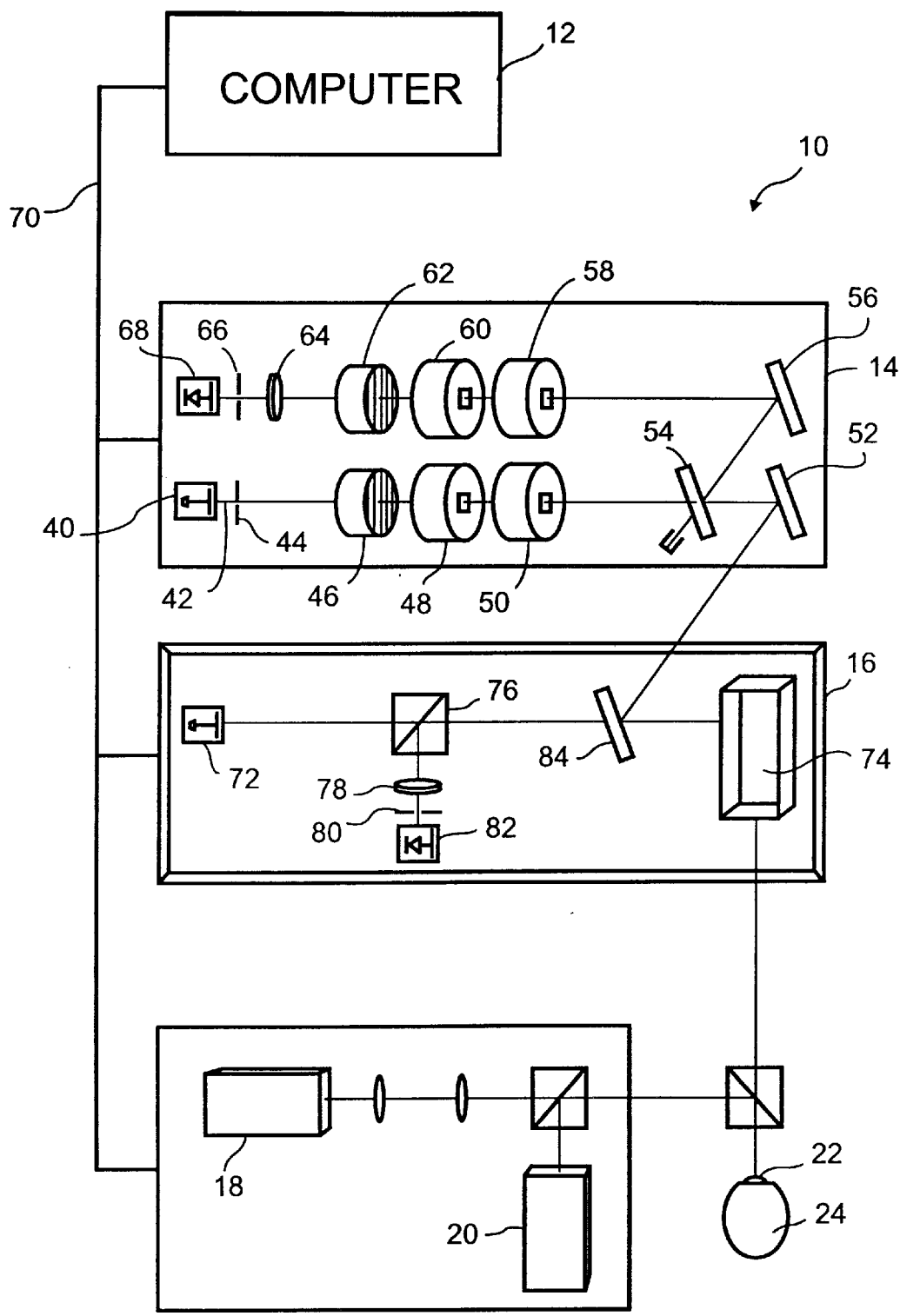
FIG. 1 is a schematic diagram of the component elements of a system in accordance with the present invention.

Referring initially to FIG. 1, the system for determining the birefringent topography of a birefringent sample is shown schematically and generally designated 10. As shown in FIG. 1, the system 10 includes a computer 12, an ellipsometer 14, a wavefront sensor 18 and a Z-tracker unit 20. As intended for the system 10 of the present invention, all of these components interact with each other in specific ways to create a birefringent topography of a birefringent sample, such as the cornea 22 of a patient's eye 24.

Figure 2:
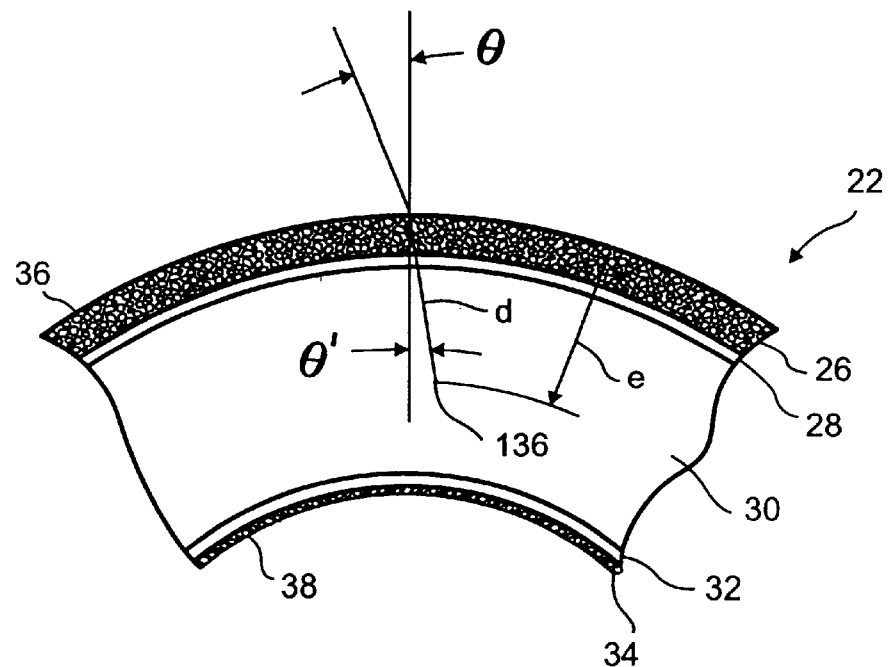
FIG. 2 is a cross sectional view of a portion of a cornea.

The cornea 22 of a patient's eye 24 has an anatomical structure as shown in FIG. 2. Specifically, the cornea 22 comprises five different layers. Going in the anterior-to-posterior direction, these layers are: the epithelium 26, Bowman's membrane 28, the stroma 30, Descemet's membrane 32 and the endothelium 34. This anatomical structure is important because it shows that the major constituency of the cornea 22 is the stroma 30. It is primarily in the stroma 30 where the stress distributions develop that affect the refractive power of the cornea 22. As mentioned above, these stress distributions manifest themselves as detectable birefringent properties.

Returning now to FIG. 1, it is to be appreciated that the ellipsometer 14 of the system 10 includes a laser diode 40 which can be selectively activated to generate a laser beam 42. When activated, the laser beam 42 is passed through a pinhole 44 and then through a polarizing unit which successively includes a polarizer 46 and two Pockel cells, Pockel cell 48 and Pockel cell 50. By selectively altering the voltage states of the Pockel cells 48, 50 four specific independent polarization states can be generated for the laser beam 42. They are: (0,0), ($\lambda/4$,0), (0,$\lambda/2$), and ($\lambda/4$,$\lambda/2$). Then, the laser beam 42, in a selected one of these polarization states is reflected out of ellipsometer 14 by mirror 52 and onto an optical path where it is subsequently focused at a point in the cornea 22 of eye 24.

After the reflection of the laser beam 42 from its focal point in the cornea 22, it is directed to reenter the ellipsometer 14. Upon reentry, the laser beam 42 is successively reflected by mirrors 52, 54 and 56 toward an analyzing unit of the ellipsometer 14. This analyzing unit includes a Pockel cell 58 and a Pockel cell 60, as well as a polarizer 62. In a manner similar to the operation of the polarizing unit, and depending on the voltage states of the Pockel cells 58, 60, the analyzing unit can generate four specific independent detection states for the laser beam 42. These are: (0,0), ($\lambda/4$,0), (0,$\lambda/2$), and ($\lambda/4$,$\lambda/2$). The laser beam 42, now affected by a particular polarization state and a particular detection state, is focused by a lens unit 64 through pinhole 66 and onto avalanche photodiode 68. The signal generated by avalanche photodiode 68 is then passed via electronics line 70 to computer 12 for analysis.

As will be appreciated by the skilled artisan, between the four polarization states and the four detection states that can be imparted on laser beam 42 by the ellipsometer 14, sixteen different readings can be taken at the point where the laser beam 42 is focused into stroma 30 of cornea 22. The mathematical manipulations which are used by computer 12 to convert these sixteen readings into a model for a meaningful birefringent analysis are fully set forth in copending U.S. patent application Ser. No. 08/709,243 which is assigned to the same assignee as the present invention and which is incorporated herein by reference.

FIG. 1 also shows that the scanning tomography unit 16 of system 10 includes a laser diode 72 which, preferably, generates a laser beam having a wavelength of about 670 nm. This laser beam is directed to scanner 74 where it is redirected toward the cornea 22 of eye 24. The reflected light is then detected by scanner 74 in a confocal arrangement. The result is an ability to detect digitized frames of two dimensional images at a repetition rate of 20 Hz. These images can then be displayed in real time by computer 12. Specifically, the reflected beam is passed from scanner 74 to mirror 76 where it is further reflected toward lens 78. The beam in then focused by lens 78 through pinhole 80 to avalanche photodiode 82. The signals from avalanche photodiode 82 are then passed via electronics line 70 to computer 12. More specifically, the size of the field scanned by scanner 74 can be set to 10°×10°, 15°×15° or 20°×20°. Further, the location of the focal plane can be adjusted between −12 and +12 diopters in increments of 0.25 diopters. The capabilities of scanner 74 also allows for a series of 32 section images at 32 equally spaced focal planes.

Figure 3:
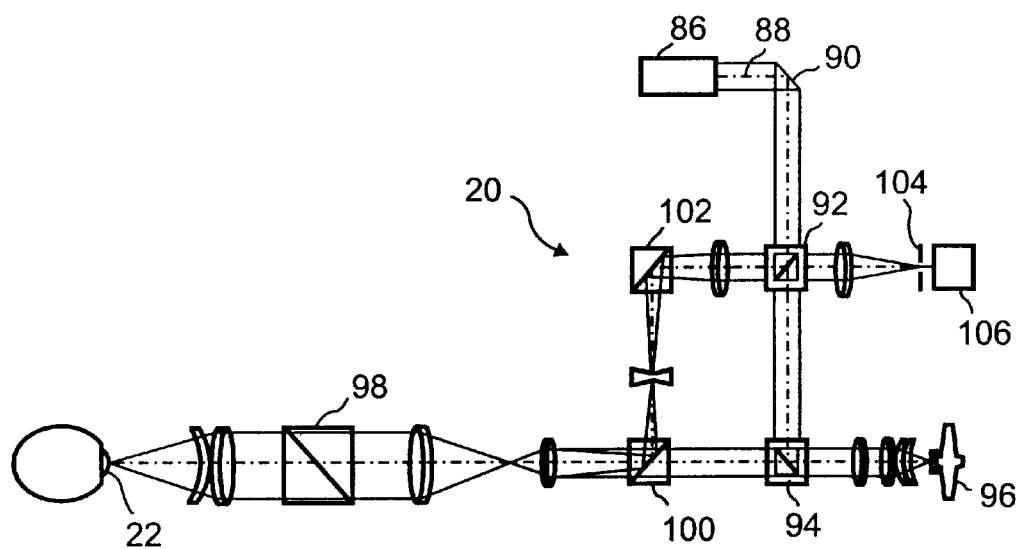
FIG. 3 is a schematic diagram of a Z-tracker unit as used with the system of the present invention.

As indicated above, the system 10 includes both a wavefront sensor 18 and a Z-tracker unit 20. To first consider the Z-tracker unit 20, refer to FIG. 3. In FIG. 3 it will be seen that the Z-tracker unit 20 includes a laser diode 86 which is used to generate a laser beam 88. This laser beam 88 is directed toward mirror 90 and through beam splitter 92 to the turning mirror 94. Thereafter, the laser beam 88 is aided by piezo-electric translator 96 and optics 98 in its direction along the optical axis of cornea 22. The light in laser beam 88 that is reflected back into the Z-tracker 20 will next pass through mirrors 100 and 102 to then be focused through pinhole 104 and onto photomultiplier tube 106. With this arrangement, it will happen that If the focus of laser beam 88 lies on the anterior surface 36 of cornea 22, the photomultiplier tube 106 will detect a maximum signal. Otherwise, the pinhole 104 will cause the laser beam 88 to fade out. As indicated in FIG. 1, these measurement signals are transmitted via electronics line 70 to the computer 12 where the exact location of anterior surface 36 is monitored and used for purposes of maintaining proper adjustment of other components in system 10.

Figure 4:
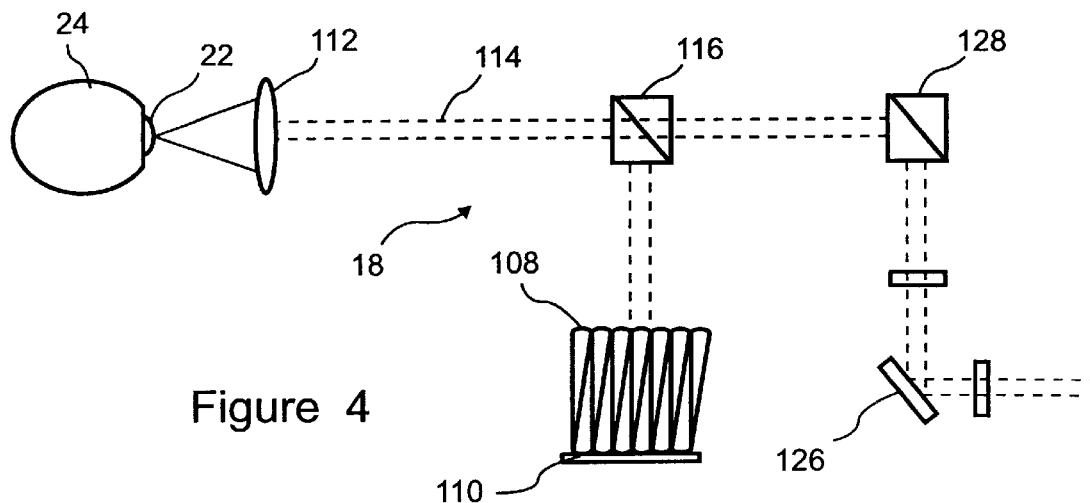
FIG. 4 is a schematic diagram of a wavefront sensor according to the present invention.

The wavefront sensor 18 of system 10 is shown schematically in FIG. 4 to include a so-called Hartmann-Shack Sensor having a lens array 108 and a pixel array 110. For the wavefront sensor 18, a lens 112 directs rays 114 that are reflected from cornea 22 toward a beamsplitter 116 where the reflected rays 114 are directed onto the lens array 108. Depending on the curvature of the cornea 22, the lens array 108 will then focus the reflected rays 114 onto various pixels in the pixel array 110 in a pattern which is indicative of the curvature of cornea 22. Just how this works will, perhaps, be best understood with reference to FIG. 5.

Figure 5:
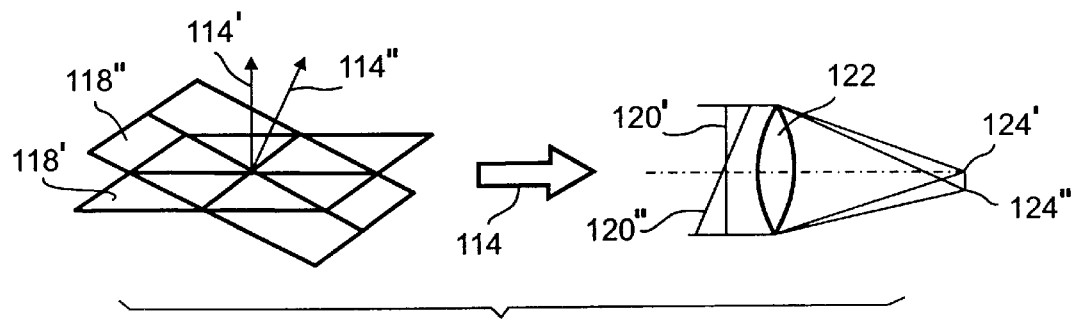
FIG. 5 is a conceptual representation of the effect of a wavefront tilt.

In FIG. 5, it will be assumed that the cornea patch 118' is from a flat portion of the cornea 22 and that the cornea patch 118" is from a tilted portion of the cornea 22. The reflected ray 114' then represents light reflected from the flat cornea patch 118' and the reflected ray 114" represents light reflected from the tilted cornea patch 118". Respectively, the rays 114' or 114" travel with other rays in wavefronts. The wavefront 120' thus represents a wavefront which includes ray 114' reflected from the flat patch 118' of cornea 22, and the wavefront 120" represents a wavefront which includes the ray 114" reflected from a tilted patch 118" of cornea 22. FIG. 5 indicates that when the wavefront 120' is focused by a lens 22 of lens array 108, the light is focused onto a pixel 124' of pixel array 110. On the other hand, when the wavefront 120" is focused by the lens 22, the light is focused onto another pixel 124". The shift in focal points from pixel 124' to 124" is indicative of the tilt, or curvature, of patch 118 on the cornea 22. As will be appreciated by those skilled in the art, a plurality of such measurements can be taken and a resultant corneal curvature, or topography, obtained. With this information, the refractive power of the cornea 22 can be determined.

In a modification to the wavefront sensor 18, an active mirror 126 can be added and optically connected with components of the sensor 18 by the beam splitter 128. When employed, the active mirror 126 can be initially calibrated as a plane surface. Using the corneal curvature measurements from pixel array 110, the active mirror 126 can then be configured to represent the initial curvature of the cornea 22. It is a simple matter to then subsequently monitor the active mirror 126 and use changes in the active mirror to indicate real time alterations in the curvature of cornea 22. This is particularly helpful during cornea sculpting operations. As indicated in FIG. 1, it is possible to connect the pixel array 110 and the active mirror 126 directly into computer 12 via electronics line 70. Thus, computer 12 can be used to monitor and control the operations set forth above.

Figure 6:
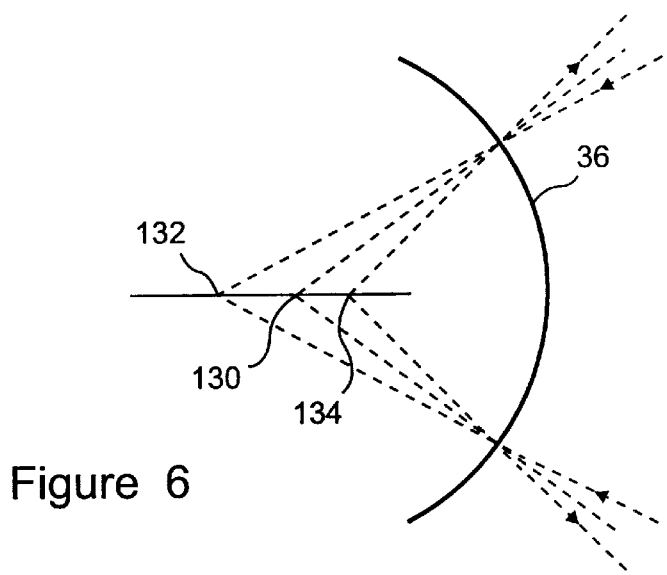
FIG. 6 is a diagram showing the relationship between surface curvature and the reflection of a lightcone.

A theoretical appreciation of the calculations involved in determining the curvature of cornea 22 can be had with reference to FIG. 6. There it will be seen that with a spherical surface for cornea 22, light incident on the anterior surface 36 of the cornea 22 will appear to be focused on and then reflected off the anterior surface 36 from an apparent source located at the point 130 in cornea 22. On the other hand, assuming the cornea 22 is not spherical and, instead, is "Steep", then light focused to a point 132 in cornea 22 will appear to be reflected from, or emit from, a point 134. Mathematically, the wavefronts here can be expressed with Zernike polynomials and optimal expansion coefficients. For purposes of the present invention, the necessary mathematical manipulations can be properly programmed into computer 12 in a manner well known in the pertinent art.

Based on information about the curvature of the cornea 22 obtained by wavefront sensor 18, an angle of incidence θ can be determined. Additionally, information about the birefringent properties of a point in the stroma 30 of cornea 22, a phase angle φ, representative of this birefringence, can be determined. With both θ and φ, the dependence of birefringence Δn(x,y) on the angle of incidence θ can be determined and, thus, corrected accordingly. The geometry involved and the import thereof on the birefringence can best be appreciated with reference back to FIG. 2 and to the relationships set forth below. As shown in FIG. 2, the distance e represents the distance between a point 136, where the birefringent measurement is to be taken, and the anterior surface 36 of the cornea 22. The distance d then represents the distance traveled by light from the anterior surface 36 to the point 136. With this in mind:

$$\Delta n(x,y) = \phi(x,y)\lambda/2\pi d(\theta)$$

Then $$\phi(x,y) = (2\pi/\lambda)d(\theta)\Delta n(x,y)$$

And (from FIG. 2)

$$d(\theta) : d = e/\cos\theta'$$

Recall that both Δn(x,y) and φ(x,y) are measurable respectively by ellipsometer 14 and wavefront sensor 18. Thus, the effect of the angle of incidence θ can also be determined.

Figure 7A:
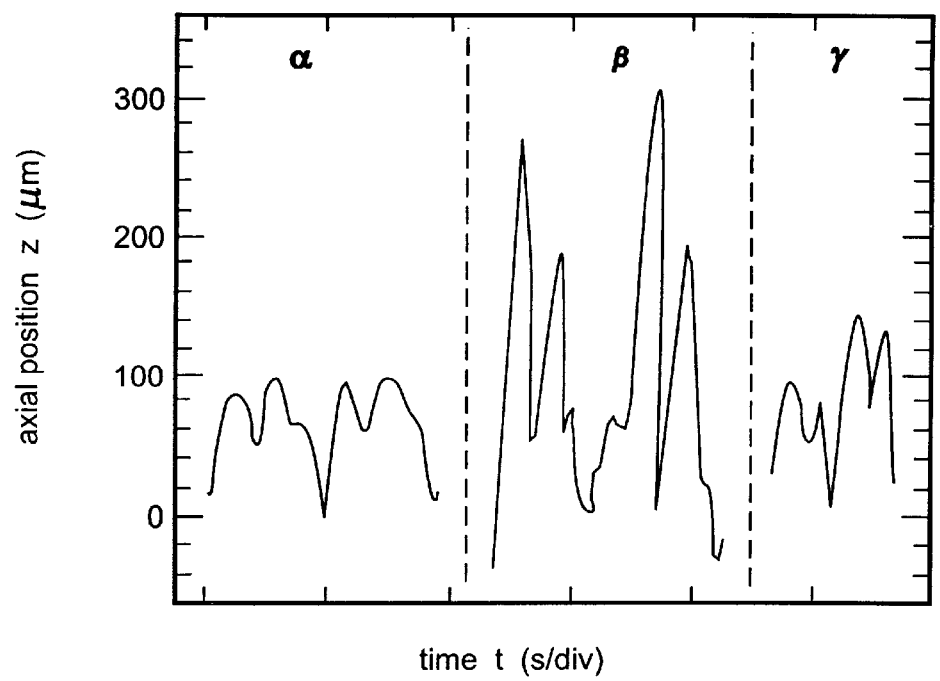
FIG. 7A is a graph comparing the axial eye movements during two heart-beat cycles of different persons.
Figure 7B:
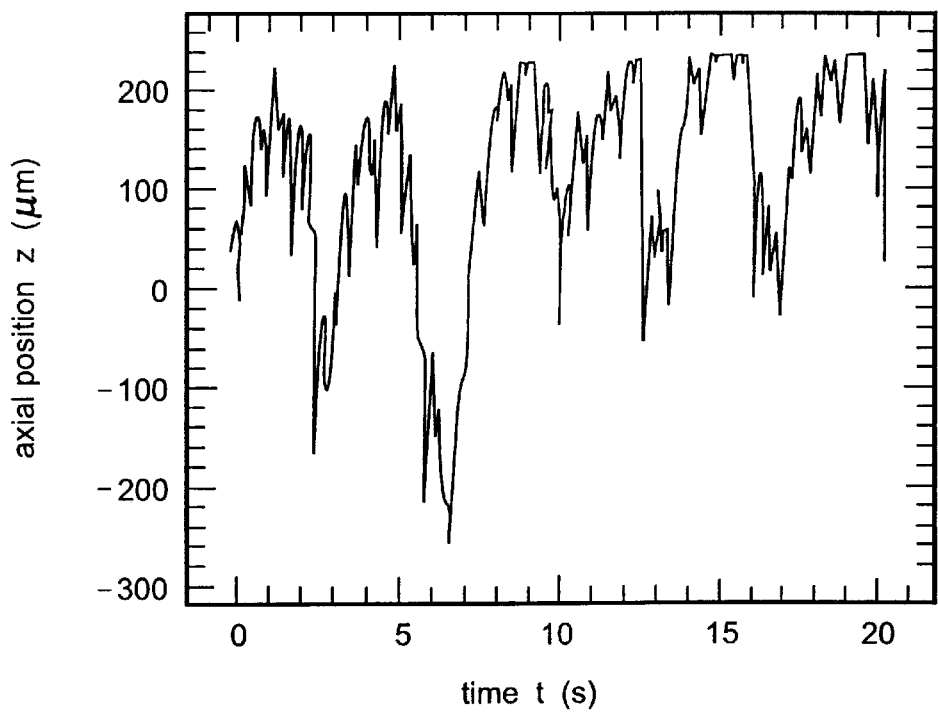
FIG. 7B is a graph depicting the influence of respiration on the axial movement of the eye.

Further refinements in the measurement of the birefringent properties and refractive power of the cornea 22 can be made by accounting for movements of the cornea 22 which are caused by patient respiration and patient heart beat. Specifically, FIG. 7A shows changes in the axial position (z) for the eye 24 of three different patients (α,β and γ) in response to their respective heart beats. Further, FIG. 7B shows changes in the axial position (z) for the eye 24 of a patient in response to his/her respiratory cycles. Such information can be preprogrammed into the computer 12 for each particular individual patient, and used during operation of the system 10. Specifically, such information can be used in conjunction with information from the Z-tracker unit 20 to anticipate and control proper placement of the ellipsometer 14 and the wavefront sensor 18 during acquisition of data by these respective components for determining the birefringent topography and the refractive power of the cornea 22.

While the particular system for determining the birefringent topography of a birefringent sample as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for determining the birefringent topography of a birefringent sample, the sample having an anterior surface separated from a posterior surface, wherein said system comprises:
 a scanning tomography unit for establishing a plane of focus within the sample;
 an ellipsometer for generating a laser beam to obtain a birefringent measurement of the sample at a point in said plane of focus;
 a topography unit for determining an angle of incidence of said laser beam relative to the anterior surface of the sample; and
 computer means for revising said birefringent measurement with said angle of incidence to obtain a corrected birefringent measurement.

2. A system as recited in claim 1 further comprising a Z-tracker unit for referencing a base datum for said system relative to said sample, and for measuring a deviation of the anterior surface of the sample from said base datum to generate an error signal, and wherein said computer means minimizes said error signal to maintain said system substantially on said base datum.

3. A system as recited in claim 2 wherein said computer means uses said deviation to refine said angle of incidence.

4. A system as recited in claim 1 wherein said ellipsometer is operated to selectively generate a plurality of said laser beams, each said beam being directed to a respective said plurality of points in said plane of focus to obtain a plurality of corrected birefringent measurements.

5. A system as recited in claim 4 wherein said scanning tomography unit is operated to selectively establish a plurality of planes of focus within the sample.

6. A system as recited in claim 5 wherein said computer means processes said plurality of corrected birefringent measurements from said plurality of planes of focus to create an optical image of the sample.

7. A system as recited in claim 1 wherein said birefringent sample is a cornea of an eye.

8. A system as recited in claim 1 wherein said birefringent topography is obtained during sculpting of the anterior surface of said sample, and wherein said topography unit determines a corneal topography, and said system further comprises:
 an active mirror;
 electronic means interconnecting said topography unit with said active mirror for reconfiguring said active mirror to calibrate the corneal topography on said active mirror; and
 computer means for evaluating changes in said active mirror to monitor changes in said corneal topography.

9. A system as recited in claim 1 wherein said scanning tomography unit comprises:
 a diode laser source for establishing said plane of focus; and
 focal means for varying said plane of focus between minus twelve diopters and plus twelve diopters (−12 and +12 diopters) in increments of one quarter diopter (0.25 diopter).

10. A system as recited in claim 9 wherein said diode laser source operates at a wavelength of six hundred and seventy nanometers (670 nm).

11. A system as recited in claim 1 wherein said ellipsometer comprises:
 a polarizing unit for generating said beam of light having a preselected irradiation state;
 an analyzing unit for receiving a reflection of said beam of light, said analyzing unit using a preselected detection state to determine a light intensity state of said beam; and
 electronic processor means in said computer means for concertedly varying said polarization state of said polarizing unit with said detection state of said analyzing unit to determine a plurality of said intensity states for said beam for use in obtaining said birefringent measurement.

12. A method for determining the birefringent topography of a birefringent sample, the sample having an anterior surface separated from a posterior surface, wherein said method comprises the steps of:
 establishing a plane of focus within the sample;
 providing a system including an ellipsometer for generating a laser beam to obtain a birefringent measurement of the sample at a point in said plane of focus, and a topography unit for determining an angle of incidence of said laser beam relative to the anterior surface of the sample;
 referencing a base datum, said base datum being taken relative to the sample;
 refining said angle of incidence according to movement of said base datum; and
 revising said birefringent measurement with said refined angle of incidence to obtain a corrected birefringent measurement.

13. A method as recited in claim 12 wherein said referencing step comprises the steps of:
 measuring a deviation of the anterior surface of the sample from said base datum to generate an error signal; and
 minimizing said error signal to maintain said system substantially fixed on said base datum.

14. A method as recited in claim 12 further comprising the step of selectively generating a plurality of said laser beams, each said beam being directed to a respective said plurality of points in said plane of focus to obtain a plurality of corrected birefringent measurements.

15. A method as recited in claim 14 wherein said scanning tomography unit is operated to selectively establish a plurality of planes of focus within the sample, and wherein said computer means processes said plurality of corrected birefringent measurements from said plurality of planes of focus to create an optical image of the sample.

16. A method as recited in claim 12 wherein said birefringent sample is a cornea of an eye.

17. A method as recited in claim 16 further comprising the step of selecting positions on the cornea for transverse cuts based on said corrected birefringent measurements.

18. A method as recited in claim 16 further comprising the steps of:
 taking corrected birefringent measurements to determine internal stresses of a recipient cornea bed;
 taking corrected birefringent measurements to determine internal stresses of a donor corneal button; and
 orienting said donor corneal button in said recipient cornea bed in accordance with said respective corrected birefringent measurements.

19. A method as recited in claim 16 further comprising the step of monitoring relaxation of internal stress distribution based on corrected birefringent measurements taken before and after surgery.

20. A method as recited in claim 16 further comprising the step of recording internal stress redistribution due to wound healing based on corrected birefringent measurements.

21. A system as recited in claim 12 wherein said birefringent sample is a cornea of an eye.

22. A system for determining the birefringent topography of a birefringent sample, the sample having an anterior surface separated from a posterior surface, wherein said system comprises:
- a laser means for establishing a plane of focus within the sample;
- a laser polarizer means for generating a laser beam to obtain a birefringent measurement of the sample at a point in said plane of focus;
- a reflection analyzing means for determining an angle of incidence of said laser beam relative to the anterior surface of the sample;
- a tracking means for referencing a base datum, said base datum being taken relative to the sample; and
- a computer means for refining said angle of incidence according to movement of said base datum, and for revising said birefringent measurement with said refined angle of incidence to obtain a corrected birefringent measurement.

23. A system as recited in claim 22 wherein said tracking means measures a deviation of the anterior surface of the sample from said base datum to generate an error signal, and said computer means minimizes said error signal to maintain said system substantially fixed on said base datum.

24. A system recited in claim 22 further wherein said laser polarizer means is an ellipsometer, and said ellipsometer selectively generates a plurality of said laser beams, each said beam being directed to a respective said plurality of points in said plane of focus to obtain a plurality of corrected birefringent measurements.

25. A system as recited in claim 24 wherein said laser means is a scanning tomography unit, and wherein said scanning tomopgaphy unit is operated to selectively establish a plurality of planes of focus within the sample, and wherein said computer means processes said plurality of corrected birefringent measurements from said plurality of planes of focus to create an optical image of the sample.

* * * * *